United States Patent [19]
Shieh

[11] Patent Number: 5,550,222
[45] Date of Patent: Aug. 27, 1996

[54] PROCESS FOR PRODUCING GAMMA-CYCLODEXTRIN

[75] Inventor: Wen Shieh, Crown Point, Ind.

[73] Assignee: American Maize-Products Company, Hammond, Ind.

[21] Appl. No.: 355,850

[22] Filed: Dec. 14, 1994

[51] Int. Cl.$^6$ .................................................. C08B 37/16
[52] U.S. Cl. ......................... 536/103; 536/124; 536/125; 536/127
[58] Field of Search .................................. 536/103, 124, 536/125, 127

[56] References Cited

U.S. PATENT DOCUMENTS 4,822,874  4/1989  Schmid et al. ........................... 536/102

FOREIGN PATENT DOCUMENTS 0614971  9/1994  European Pat. Off. .

OTHER PUBLICATIONS

J. A. Rondleman, "Enhanced Production of Cyclomaltooctrase (Y–cyclodextrin) through Selective Complexation with $C_{12}$ Cyclic Compounds" Carbohydrate Research 230 (1992) 343–359.

Primary Examiner—Nathan M. Nutter
Attorney, Agent, or Firm—Lucas & Just

[57] ABSTRACT

A process for preparing cyclooctaamylose by enzymatic reaction of starch hydrolysate with cyclodextrin glycosyltransferase in the presence of at least two complexing agents. The first is either an aliphatic ketone or an aliphatic alcohol and the second is a cyclic compound which has 12 atoms.

17 Claims, No Drawings

PROCESS FOR PRODUCING GAMMA-CYCLODEXTRIN

This invention relates to cyclodextrin and more specifically to a process for the manufacture of gamma-cyclodextrin.

Conventionally, cyclodextrin is produced by the action of an enzyme, cyclodextrin glycosyltransferase, on a starch substrate, at the appropriate pH and temperature for the enzyme. The enzyme treatment of the starch substrate generally produces at least three cyclodextrins, alpha-, beta- and gamma-cyclodextrin, with gamma-cyclodextrin usually being least favored. Alpha-cyclodextrin is a cyclic compound comprising six anhydroglucose units bonded by alpha 1–4 bonds. Beta-and gamma-cyclodextrin, like alpha-cyclodextrin, are cyclic compounds of anhydroglucose bonded by alpha 1–4 bonds and having seven and eight members in the ring, respectively.

Oftentimes, a complexant is employed during the enzymatic conversion of a starch substrate to cyclodextrin to enhance production. The complexant forms insoluble complexes with the cyclodextrin thereby shifting the equilibrium and causing more cyclodextrin to be produced by the enzyme. It is also known that certain complexants increased production of only one cyclodextrin. For example, U.S. Pat. No. 4,822,874 teaches the use of certain ringed compounds having between 13 and 24 atoms in the ring to increase production of gamma-cyclodextrin. J. A. Rendleman, in his article entitled "Enhanced Production of Cyclomaltooctaose (gamma-cyclodextrin) through Selective Complexation with $C_{12}$ Cyclic Compounds", Carbohydrate Research 230 (1992) 343–359, has suggested using $C_{12}$ cyclic compounds such as cyclododecanone, cyclodedecanol, cyclododecane methanol, cyclodedecyl methyl ether and cyclododecane to increase the production of gamma-cyclodextrin. However, according to Rendleman's article the reaction was complete in seven to fifteen days. Such a long reaction period is not acceptable for commercial applications.

Gamma-cyclodextrin is more water soluble than alpha- or beta-cyclodextrin and has a larger hydrophobic torus interior than alpha- or beta-cyclodextrin. These properties make gamma-cyclodextrin extremely attractive for use in the cosmetic, pharmaceutical, and food industry.

There is a need for an efficient process for producing gamma-cyclodextrin. Such a process should produce high yields of gamma-cyclodextrin in relatively short periods of time, i.e. 1–2 days.

A process for producing gamma-cyclodextrin in large quantities, 30–40% of the reaction product, and in a relatively short period of time, less than 72 hours, has now been discovered. The process of the present invention employs at least two complexants, simultaneously, during the enzyme conversion of a starch substrate to cyclodextrin. It has been found that by using at least two complexants in accordance with the present invention that relatively high yields of gamma-cyclodextrin have been obtained.

In the present invention, one of said complexants is an aliphatic alcohol and/or an aliphatic ketone while the second complexant is a ringed compound having only twelve members in the ring; $C_{12}$ cyclic compounds are preferred. More than two complexants can be used in the present invention. For example, two cyclic compounds having 12 atoms in the ring can be used in conjunction with the alcohol or ketone.

In any event, at least two complexants must be used in accordance with the present invention wherein one of said complexants is a ringed compound having 12 atoms in the ring and the other complexant is selected from the group consisting of aliphatic alcohols and aliphatic ketones.

More specifically, the process of the present invention comprises: a) treating an aqueous slurry of starch substrate with a cyclodextrin glycosyltransferase in the presence of at least two complexing agents, a first complexing agent selected from the group consisting of aliphatic ketones and aliphatic alcohols, and a second complexing agent being a ringed compound having twelve atoms in the ring and having a formula:

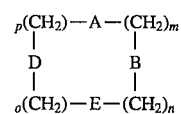

wherein,

A, B, D and E represent a substituent, independently selected from one another, selected from the group consisting of

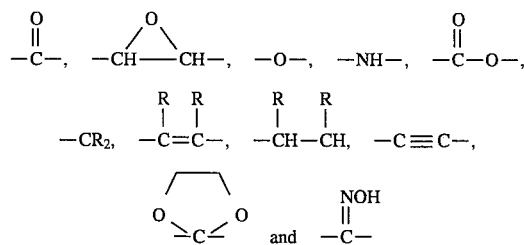

wherein,

R is a substituent selected from the group consisting of a hydrogen atom, an alkyl radical, an hydroxyl radical, an alkoxy radical and a carboxyl radical, m, n, o, p are integers each being within the range of 0 to 8, with the proviso that the number of atoms forming the ring is 12; and b) recovering cyclooctaamylose.

Aliphatic alcohols which are suitable for the present invention have a formula of $C_nH_{2n+1}OH$ wherein n=1 to 6. More specifically, suitable aliphatic alcohols include butanol, ethanol and propanol. Good results have been obtained with 1-butanol.

Aliphatic ketones which are suitable for the present invention have a formula of $R_1$—CO—$R_2$ wherein $R_1$ and $R_2$ are each either straight or branched alkyl groups having anywhere from 1 to 6 carbons. More specifically, suitable aliphatic ketones include methylethylketone, methylisobutyl ketone and acetone. Good results have been obtained with methylethylketone.

Ringed compounds having 12 atoms in the ring which are suitable for the present invention have the following formula:

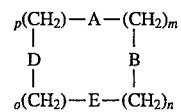

wherein,

A, B, D and E represent a substituent, independently selected from one another, selected from the group consisting of

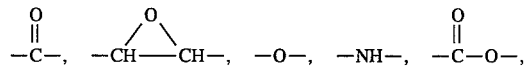

-continued

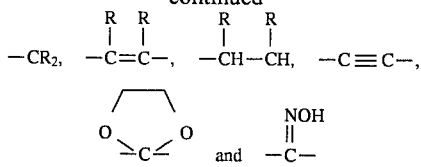

wherein,

R is a substituent selected from the group consisting of a hydrogen atom, an alkyl radical, an hydroxyl radical, an alkoxy radical and a carboxyl radical, m, n, o, p are integers each being within the range of 0 to 8, with the proviso that the number of atoms forming the ring is 12.

The preferred 12 membered ring is a $C_{12}$ cyclic compound, however, the 12 member ringed compound need not have only carbon in the ring. For example it can include a nitrogen or an oxygen, as well as both single, double and triple bonds. Compounds having a 12 membered ring which are suitable in the present invention include cyclododecanone, cyclododecanol, cyclodedecane methanol, cyclododecyl methyl ether, cyclododecane, 2,3-cyclododecenopyridine, cyclododecone epoxide and mixtures thereof. Good results have been obtained with cyclododecanone with a mixture of cyclododecanone and cyclododecanol.

The amount of combined complexants, first and second complexants, which are suitable for use in the present invention is about 3% to about 15% based on the weight of the starch substrate. More preferably, the combined amount of complexants used in the present invention is about 3% to about 12%. Good results have been obtained with about 6% of combined complexants.

The total amount of the two complexants employed depends upon the amount of the ringed compound employed in the process of the present invention. The amount of twelve membered ringed complexant used in the present invention is greater than about 2% by weight of starch substrate. At about 10% by weight of starch substrate, the ringed compound appears to be present in excess. Thus, it is preferred to use about 2% to about 10% by weight of the ringed compound, and, more preferably, about 3 to about 8% by weight of ringed compound. Good results have been obtained with about 3%.

The amount of alcohol or ketone depends upon the amount of ringed compound. The amount of alcohol or ketone must be enough to dissolve the ringed compound. In other words, the first complexant acts as a solvent for the second complexant. It has been found that about 1% by weight starch substrate of said first complexant is enough to dissolve about 2 to about 3% of said second complexant. Thus, the amount of said first complexant employed is about 1% to about 5% by weight of starch substrate and more preferably about 1% to about 4%. Good results have been obtained with about 3%.

The starch substrates suitable for use in accordance with the present invention are gelatinized starch and starch hydrolysates having a dextrose equivalent (DE) of about 1 to about 15. More preferably the starch substrate is a starch hydrolysate having a DE of about 3 to about 10 and good results have been obtained with a starch hydrolysate having a DE of about 5 to about 8.

The starch itself can be from any source to include corn, wheat, rice and potato. Corn starch has been found to be a good source for the present invention.

The concentration of starch substrate in the aqueous slurry is about 5% to about 40% by weight of the slurry and good results have been obtained with a slurry having a starch substrate in the amount of about 30% by weight.

The enzyme, cyclodextrin glycosyltransferase, suitable for the present invention can be from any conventional source such as *Bacillus macerans, Bacillus stearothermophilus*, and *Bacillus circulans*. The amount of enzyme used is based on the activity of the enzyme and the amount of starch substrate. Suitable amounts include enzyme to starch weight ratio of about 1:2,000 to 1:50,000.

The temperature during the treatment step is optimized for the enzyme employed. The temperature during treatment is suitably about 30° C. to about 60° C. and more preferably about 30° C. to about 50° C. Good results have been obtained at about 40° C. Suitable pH ranges between about 4 to about 9 and more preferably about 6 to about 8. Good results have been obtained at a pH of about 7.

During the treatment, it is preferred to add a small amount of calcium chloride to stabilize the enzyme, and specifically about 5 mM to about 15 mM. Good results have been obtained when the concentration of the calcium chloride is about 10 mM.

The treatment step is conducted in a conventional manner using conventional equipment. Specifically the appropriate amount of the enzyme and appropriate amount of the two complexants are added to a tank of aqueous starch substrate at the appropriate pH and temperature and containing the optimal calcium chloride. The tank is preferably equipped with an impeller to mildly agitate the solution during treatment. The complexants form insoluble complexes with the gamma-cyclodextrin which are removed from the tank in a conventional manner using conventional equipment. For example, the insoluble complex is removed from the tank by decanting, filtering or centrifugation.

After the complex is removed from the tank the complex is separated into its individual components, gamma-cyclodextrin and complexants, in a conventional manner using conventional equipment. Suitable means include boiling or heating a mixture of complex and water.

In order to add the two complexants to the aqueous slurry of starch substrate, the second complexant is dissolved into the first complexant and the solution of the two complexants is added to the slurry. The solution of the two complexants is made in a conventional manner using conventional equipment. The present invention has been found to produce 30% to 40% gamma-cyclodextrin based on the weight of starch substrate.

Other conventional methods can be employed to further purify the gamma-cyclodextrin.

These and other aspects of the present invention may be more fully understood by reference to the following examples.

Example 1

This example compares the present invention to the prior art methods without complexant and an individual $C_{12}$ cyclic compound as taught by Rendleman.

Four batches containing 100 grams of a starch hydrolysate, DE 5-8, at a pH of 7, a temperature of 40° C. and containing 10 mM calcium chloride were treated with a cyclodextrin glycosyltransferase and complexant or without complexant as listed below. The yields over a 3-day period are also listed below as well as the amount of complexant.

|  | GCD (% Yield) | BCD (% Yield) |
| --- | --- | --- |
| No-Complexant (Prior Art) | | |
| 24 hours | 1.45 | 2.18 |
| 48 hours | 1.57 | 2.24 |
| 72 hours | 1.57 | 2.24 |
| Complexant: Cyclododecanone (3 grams) (Prior Art) | | |
| 24 hours | 19.2 | 4.3 |
| 48 hours | 20.0 | 4.7 |
| 72 hours | 20.1 | 4.7 |
| Complexant: Methylethylketone (3 grams) and Cyclododecanone (3 grams) (Present Invention) | | |
| 24 hours | 34.4 | 4.7 |
| 48 hours | 42.4 | 6.3 |
| 72 hours | 42.4 | 6.9 |
| Complexant: 1-Butanol (3 grams) and Cyclododecanone (3 grams) (Present Invention) | | |
| 24 hours | 34.5 | 5.0 |
| 48 hours | 41.1 | 6.7 |
| 72 hours | 43.5 | 7.5 |

As can be seen the present invention produced superior results to that of the prior art.

It will be understood that the claims are intended to cover all changes and modifications of the preferred embodiments of the invention herein chosen for the purpose of illustration which do not constitute a departure from the spirit and scope of the invention.

What is claimed is:

1. A process for preparing cyclooctaamylose comprising the steps of:

a) treating an aqueous slurry of starch substrate with a cyclodextrin glycosyltransferase in the presence of two or more complexing agents, a first complexing agent being an aliphatic ketone or an aliphatic alcohol; and a second complexing agent having twelve atoms in the ring and having a formula $$\begin{array}{c} {}_p(CH_2)-A-(CH_2)_m \\ | \quad\quad\quad\quad | \\ D \quad\quad\quad\quad B \\ | \quad\quad\quad\quad | \\ {}_o(CH_2)-E-(CH_2)_n \end{array}$$

wherein,

A, B, D and E represent a substituent, independently selected from one another, selected from the group consisting of

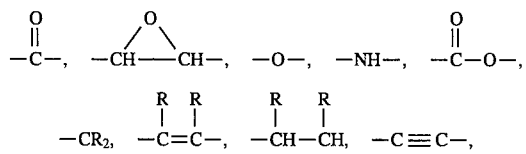

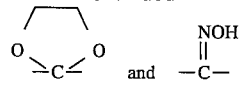

wherein

R is a substituent selected from the group consisting of a hydrogen atom, an alkyl radical, an hydroxyl radical, an alkoxy radical and a carboxyl radical, m, n, o, p are integers each being within the range of 0 to 8, with the proviso that the number of atoms forming the ring is 12; and b) recovering cyclooctaamylose.

2. The process of claim 1 wherein said aliphatic ketone is selected from the group consisting of methylethylketone, methylisobutyl ketone and acetone.

3. The process of claim 1 wherein said aliphatic alcohol is selected from the group consisting of butanol, ethanol and propanol.

4. The process of claim 1 wherein said second complexing agent is selected from the group consisting of cyclododecanone, cyclododecanol, cyclodedecane methanol, cyclododecyl methyl ether, cyclododecane, 2,3-cyclododecenopyridine, cyclododecone epoxide and mixtures thereof.

5. The process of claim 1 wherein said starch substrate is a starch hydrolysate having a DE of about 5 to about 8.

6. The process of claim 1 wherein said treatment step is conducted at a pH of about 6 to about 8.

7. The process of claim 1 wherein said treatment is conducted at a temperature of about 30° C. to about 60° C.

8. The process of claim 1 wherein said first complexing agent is methylethylketone and said second complexing agent is cyclododecanone.

9. The process of claim 1 wherein said first complexing agent is butanol and said second complexing agent is cyclododecanone.

10. The process of claim 1 wherein said starch substrate is a starch hydrolysate having a DE of about 5 to about 8 and said first complexing agent is selected from the group consisting of methylethylketone and butanol and said second complexing agent is cyclododecanone.

11. The process of claim 10 wherein said treatment is conducted at a pH of about 7.

12. The process of claim 10 wherein the temperature during treatment is about 40° C.

13. The process of claim 11 wherein the temperature during treatment is about 40° C.

14. The process of claim 1 wherein said aliphatic alcohol has a formula of $C_nH_{2n+1}OH$ wherein said n=1 to 6.

15. The process of claim 1 wherein said aliphatic ketone has a formula of

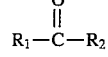

wherein $R_1$ and $R_2$ are straight or branched alkyl chains of $C_1$ to $C_6$.

16. The process of claim 1 wherein said two complexing agent are present in an amount of about 2% to about 15% by weight of said starch substrate.

17. The process of claim 1 wherein said first complexing agent is present in an amount of about 2% to about 10% by weight of said starch substrate.

* * * * *